United States Patent
Appel et al.

(10) Patent No.: US 6,579,530 B2
(45) Date of Patent: Jun. 17, 2003

(54) COSMETIC POWDER PENCIL OR POWDER CHALK

(75) Inventors: Reiner Appel, Oberasbach (DE); Joachim Kinzel, Stein (DE); Harald Von Godin, Oberasbach (DE); Gerhard Lugert, Nürnberg (DE)

(73) Assignee: Faber-Castell AG, Stein (DE)

( * ) Notice: Subject to any disclaimer, the term of this patent is extended or adjusted under 35 U.S.C. 154(b) by 0 days.

(21) Appl. No.: 10/125,656

(22) Filed: Apr. 19, 2002

(65) Prior Publication Data

US 2003/0068288 A1 Apr. 10, 2003

(30) Foreign Application Priority Data

Apr. 19, 2001 (DE) .......................... 101 19 292

(51) Int. Cl.⁷ .......................... A61K 7/00; A61K 7/021; A61K 7/06; A61K 9/00
(52) U.S. Cl. ................ 424/401; 424/63; 424/70.6; 424/400; 424/DIG. 5
(58) Field of Search ................ 424/400, 401, 424/63, 70.6, DIG. 5

(56) References Cited

U.S. PATENT DOCUMENTS 6,461,067 B1 * 10/2002 Beck et al. .................... 401/7
2002/0000012 A1 * 1/2002 Schmenger et al. ........... 8/405

* cited by examiner

*Primary Examiner*—Jose' G. Dees
*Assistant Examiner*—Marina Lamm
(74) *Attorney, Agent, or Firm*—Venable, LLP; Marina V. Schneller

(57) ABSTRACT

A make-up stick or crayon contains the following essential components:

polyether-1: 3.0 weight %
mica: 69.0 weight %
PMMA (polymethylmethacrylate): 28.0 weight %

Based on this starting formulation, the powdery components can be mixed by adding water in amounts of 20–40 weight %. The homogeneous mass is subsequently extruded to form a rope which is then cut into lengths.

14 Claims, No Drawings

COSMETIC POWDER PENCIL OR POWDER CHALK

CROSS REFERENCE TO RELATED APPLICATION

This application claims the benefit of priority of the German patent application 10119292.4, filed Apr. 19, 2001 which is relied upon and incorporated by reference herein.

BACKGROUND OF THE INVENTION

The invention relates to powder pencil leads, used in particular for cosmetic pencils and powder chalks. The latter are also known as soft pastel chalks. A cosmetic pencil provided with a lead in the form of a shaped body with porous composition that consists of mica, magnesium myristate as adhesion promoter and bentonite is described in DE 25 40 877 C2. A mica-containing and talcum-containing powder pencil lead, which contains spherical cellulose powder as binder, is known from reference EP 0 432 279 A1. In the same way as gypsum-containing leads (U.S. Pat. No. 4,624,273) or tri-calcium phosphate containing leads (DE 33 47 756 C2), these leads also have a porous composition. Owing to their low mechanical strengths, the production of these leads is problematic because the danger of a lead breakage is very high. A further disadvantage is that the leads break easily during the application to the skin and during the sharpening and have a tendency to crumble.

Thus, it is the object of the invention to propose a lead for cosmetic powder pencils and powder chalks, used for cosmetic purposes or for pastel drawings on paper or other surfaces. This lead distinguishes itself through increased strength and flexibility during the production, a very soft non-crumbling powder release during the application and the fact that it can be sharpened easily with standard sharpening devices.

SUMMARY OF THE INVENTION

This object is solved in that a copolymer is used as thickening agent, which contains polyoxyethyleneglycol-polymer (PEG) with 5 to 300 $CH_2$—$CH_2$—O monomers and also contains tetramethoxy-methylglycouril monomers. A copolymer of PEG-180 (q.v. [quod vide]=see previous), Dodoxynol-5, PEG-25-tristyrylphenol and tetramethoxymethylglycouril monomers is preferably used as thickening agent. According to the INCI[1] nomenclature, this substance is also referred to as "Polyether-1." The aforementioned copolymer component Dodoxynol-5 is PEG-5 dodecylphenylether.

[1]Translator's Note: INCI=International Nomenclature of Cosmetic Ingredients

Surprisingly, the use of associative thickening agents of this type not only has a thickening and emulsifying effect on the powdery components laced with water during the production, but also results in noticeably improved flexibility of the extruded lead ropes as well as uniform extrudability during the production as compared to the prior art. In the process, strength values can be achieved that match those of brittle and inflexible leads used for comparison, which contain bentonite (example V). By adding a very small amount of organic binder, e.g. sodium alginate, it is possible to nearly double the breaking strength without this reducing the mechanical properties such as very soft applicability, excellent sharpening ability and flexibility of the initially water-containing lead rope.

In particular polymethylmethacrylate and mica are suitable as powder-containing filler materials. Mica with a small share of silica added to it (0.5 to 7 weight %) is advantageously used. Mixtures of the aforementioned filler materials surprisingly have distinguished themselves through a very soft, powdery release and can be produced without problems. The starting materials mixed with water, in the simplest case referring to thickening agents and filler materials, can be processed into masses with a homogeneous distribution of the filler material particles. These masses keep their consistency even during the extrusion process, meaning there is no separation between the thickening agent phase and the solid-material phase. In general terms, a mixture of a filler material with essentially spherical particles and a filler material with platelet-shaped particles is used. Particularly good results are obtained with potash (muscovite).

Adding small amounts (<10%) of clay, kaolin, talcum, magnesium myristate or calcium stearate in particular can influence the release of the mass during the application as well as the mechanical strength. Wetting agents such as disodium-laureth-sulfosuccinate (INCI name), for example, can be used as auxiliary substances for extruding the leads and as adhesion promoters. To improve the sliding ability during the application and to improve the adhesive strength of the powder, as well as to reduce the formation of fissures in the leads during the drying process, small amounts (<10%) of waxes, fats, oils (e.g. castor oil) or emulsifiers can be added. Hydrogenated palm kernel glycerides, hydrogenated palm glycerides are listed as examples. Protective substances such as lanolin, aloe vera, tocopherol and others as well as preserving agents or aromatic substances can also be added.

DETAILED DESCRIPTION

The following is a basic formula for producing powder leads and powder chalks:

Basic Formula:

thickening agent: 0.1–5 weight % organic binders: 0–3 weight % filler materials: 40–95 weight % wetting agents: 0–10 weight % waxes, fats, oils, emulsifiers: 0–10 weight % colorants: 0–50 weight % additives: (e.g. aromatic agents, preserving agents protective substances) 0–5 weight %

A lead or chalk containing only the "required components" of the basic formula has the following composition:

Example 1:

polyether-1: 3.0 weight % mica: 69.0 weight %

PMMA (polymethylmethacrylate): 28.0 weight %

With this basic formula, leads for cosmetic purposes were produced as follows:

The powdery components were mixed homogeneously inside a kneading machine or mixer by adding water in amounts of 20–40 weight %. The homogeneous mass was subsequently extruded to form a rope with a diameter of 6 mm and was then cut into lengths. The lead sections obtained in this way were dried at a moderate temperature (20–70° C.). Three different lead masses or leads as well as a lead used for comparison (example V) were produced in this way. The respective lead composition and several characteristic properties follow from the table below:

| raw material | example V for comparison black lead | example 2 black lead | example 3 black lead | example 4 yellow lead |
|---|---|---|---|---|
| mica 97–99%, silica 1–3% (CAS 12001-26-2, 7631-86-0) | 20.0 | 20.0 | 20.0 | 20.0 |
| polymethyl-methacrylate | 40.0 | 40.0 | 40.0 | 50.0 |
| disodium laureth sulfo-succinate | 5.0 | 5.0 | 5.0 | 6.0 |
| hydrogenated palm kernal glycerides, hydrogenated palm glycerides (CAS 67701-26-2) | 4.0 | 4.0 | 4.0 | — |
| iron oxide black CI 77499 | 30.0 | 30.0 | 30.0 | — |
| titanium dioxide CI 77891 | — | — | — | 15.0 |
| FD & C yellow No. 5. A1 lake CI 19140:1 | — | — | — | 2.4 |
| iron oxide yellow CI 77492–77491 | — | — | — | 0.5 |
| breaking strength for dry leads [N] at 14.8 mm support spacing for lead | 6 | 5 | 9 | 6 |
| extrudability | poor | good | good | good |
| flexibility of freshly extruded lead | poor | high | high | high |

Of course, it is possible to produce leads or chalks with diameters that are smaller or larger than 6 mm with the above-provided basic formula. Also conceivable are leads and chalks having diameters of approximately 3 to 12 mm.

What is claimed is:

1. Cosmetic powder pencil lead or chalk containing a filler material and a thickener, wherein
    the thickening agent is a copolymer composed of at least one polyoxyethyleneglycol-polymer (PEG) with 5 to 300 $CH_2$—$CH_2$—O-monomers and tetramethoxy methylglycouril-monomers.

2. A cosmetic powder pencil lead or chalk according to claim 1,
    which comprises a copolymer of PEG-180, Dodoxynol-5, PEG-25-tristyrylphenol and tetramethoxymethylglycouril-monomers.

3. A cosmetic powder pencil lead or chalk according to claim 2, which comprises Polyether-1 (INCI name).

4. A cosmetic powder pencil lead or chalk according to claim 1, which comprises particles of PMMA (polymethylmethacrylate) as filler material.

5. A cosmetic powder pencil lead or chalk according to claim 1, which, comprises mica as additional filler material.

6. A cosmetic powder pencil lead or chalk according to claim 1, which comprises silica as additional filler material.

7. A cosmetic powder pencil lead or chalk according to claim 1, which comprises the following formulation:
    thickening agents: 0.1–5 weight %
    organic binders: 0–3 weight %
    filler materials: 40–95 weight %
    wetting agents: 0–10 weight %
    waxes, fats, oils, emulsifying agents: 0–10 weight %
    colorants: 0–50 weight %
    additives selected from the group consisting aromatic agents, of preserving agents, protective substances: 0–5 weight %.

8. A cosmetic powder pencil lead or chalk according to claim 7, which comprises PMMA admixed with silica or PMMA admixed with silica and mica, and is characterized by a ratio of PMMA to mica or a ratio of PMMA to a mixture of mica and silica which comprises a range defined by 35 to 45/55 to 65.

9. A cosmetic powder pencil lead or chalk according to claim 7, which comprises silica in an amount of 0.5 to 7.0 weight %, in combination with mica and wherein the said amount relative to the total amount is of mica and silica.

10. A cosmetic powder pencil lead or chalk according to claim 1, which comprises an organic binder.

11. A cosmetic powder pencil lead or chalk according to claim 10, which comprises sodium alginate.

12. A cosmetic powder pencil lead or chalk according to claim 1, which comprises disodium-laureth-sulfosuccinate as wetting agent.

13. A cosmetic powder pencil lead or chalk according to claim 1, which comprises hydrogenated palm kernel glycerides, hydrogenated palm glycerides as fatty acid derivative.

14. A cosmetic powder pencil lead or chalk according to claim 7, which comprises PMMA admixed with silica or PMMA admixed with silica and mica, and is characterized by a ratio of PMMA to mica a ratio of PMMA to a mixture of mica and silica which comprises a range defined by 35–45/55–65;
    which comprises silica in an amount of 0.5 to 7.0 weight %, relative to the total amount of mica and silica;
    which further comprises an organic binder;
    sodium alginate;
    disodium-laureth-sulfosuccinate as wetting agent; and
    at lease one fatty acid derivative selected from the group consisting of hydrogenated palm kernel glycerides, and hydrogenated palm glycerides.

* * * * *